(12) United States Patent
Dean

(10) Patent No.: US 10,172,352 B1
(45) Date of Patent: Jan. 8, 2019

(54) METHOD FOR AMELIORATION OF THE GLYPHOSATE EFFECT

(71) Applicant: LidoChem, Inc., Hazlet, NJ (US)

(72) Inventor: Frank William Dean, Spring, TX (US)

(73) Assignee: LIDOCHEM, INC., Hazlet, NJ (US)

( * ) Notice: Subject to any disclaimer, the term of this patent is extended or adjusted under 35 U.S.C. 154(b) by 0 days.

(21) Appl. No.: 13/831,759

(22) Filed: Mar. 15, 2013

Related U.S. Application Data

(63) Continuation-in-part of application No. 12/983,129, filed on Dec. 31, 2010, now abandoned.

(60) Provisional application No. 61/335,156, filed on Dec. 31, 2009, provisional application No. 61/766,124, filed on Feb. 19, 2013.

(51) Int. Cl.
*A01N 57/00* (2006.01)
*A01N 37/44* (2006.01)

(52) U.S. Cl.
CPC .................................. *A01N 37/44* (2013.01)

(58) Field of Classification Search
None
See application file for complete search history.

(56) References Cited

U.S. PATENT DOCUMENTS 3,536,471 A * 10/1970 Ashley ................................ 71/8
4,267,355 A * 5/1981 Scott et al. ...................... 560/43
6,908,882 B1 * 6/2005 Becher et al. ............. 504/116.1
8,461,085 B2 * 6/2013 Weston et al. ................ 504/314
2012/0015806 A1 * 1/2012 Paikray et al. ............... 504/117

FOREIGN PATENT DOCUMENTS

| BE | 847891 | * | 5/1977 |
| CN | 101440007 | * | 5/2009 |
| JP | 2007-191403 | * | 2/2007 |
| WO | WO 2005077171 | * | 8/2005 |

OTHER PUBLICATIONS

Low et al.(The effect of *Saccharomyces cerevisiae* on the stability of the herbicide glyphosate during bread leavening, Letters in Applied Microbiology 2005, 40, 133-7).*
Siqueira et al. (Physiological suppression of phytotoxic effects of glyphosate in soybean explant, Revista Brasileira de Fisiologia Vegetal, 1998, 10(2), 137-142).*
Shaban et al. (Recovery of faba bean(*Vicia faba* L.) plants as affected by glyphosate, J. of Agronomy and Crop Science, 1987, 158(5), 294-303).*
Gresshoff (Growth inhibition by glyphosate and reversal of its action by phenylalanine and tyrosine, Australian Journal of Plant Physiology, 1979, 6(2), 177-85).*

* cited by examiner

*Primary Examiner* — Alton N Pryor
(74) *Attorney, Agent, or Firm* — Karen B. Tripp

(57) ABSTRACT

A method to overcome the unintended effects of repeated glyphosate applications and improve the health and vigor of plants, by remediating the soil with soil remediating microbes and replenishing the amino acid pool by applying foliar essential amino acids.

10 Claims, 5 Drawing Sheets

Nurtasmart's ability to grow in high concentrations of glyphosate.

Nurtasmart's ability to grow in high concentrations of glyphosate with soil.

Fungal and Bacterial growth inhibition with the addition of essential amino acids to the agar media.

Photo shows visual morphology changes in flowering and leaf color, size, shape, and number.

METHOD FOR AMELIORATION OF THE GLYPHOSATE EFFECT

RELATED PATENT APPLICATION

This patent application claims priority from U.S. patent application Ser. No. 12/983,129, filed Dec. 31, 2010, pending, which claims priority from U.S. Provisional Patent Application No. 61/335,156, filed Dec. 31, 2009, and U.S. Provisional Patent Application No. 61/766,124, filed Feb. 19, 2013.

BACKGROUND OF THE INVENTION

I. Field of the Invention

This invention relates to the amelioration of glyphosate affects on plants, soils and microorganisms.

II. Description of Relevant Art

Glyphosate, N-(phosphonomethyl)glycine, is the most used herbicide in the history of agriculture. Weed management programs in glyphosate resistant (GR) field crops have provided highly effective weed control. However, this broad-spectrum, systemic herbicide has had unintended effects on nutrient availability and disease severity, thereby threatening its sustainability. A significant increase in disease severity associated with the wide spread application of the glyphosate herbicide can be the result of direct glyphosate-induced weakening of plant defenses and increased pathogen population and virulence.

Indirect effects of glyphosate on disease susceptible plants result from immobilization of micronutrients, reduced growth and vigor of plants, accumulation of glyphosate in plant tissues, and altered soil micro fauna and flora. In order to improve economic yield of crops it is necessary to overcome the unintended effects of repeated glyphosate applications.

U.S. Pat. No. 6,908,882 issued to Becher, et al, discusses that the addition to a glyphosate herbicide of a composition having at least two surfactants, one of which has a cationic or protonatable amino group and the other of which is an anionic N-acyl derivative of an amino acid or a salt thereof, unexpectedly provides herbicidal activity that is synergistically greater than that provided by either one of these surfactants alone at an equal weight ratio of total surfactant to glyphosate. This does not however change or diminish the unintended effects of glyphosate.

U.S. Pat. No. 5,863,863 Hasebe, et al. discusses a liquid enhancer composition for glyphosate comprising specific tertiary amine and a derivative thereof, at least one oxalic acid or a salt thereof selected from the group consisting of oxalic acid, potassium oxalate, alkanolamine salts of oxalic acid, and lower alkylamine salts of oxalic acid, wherein the ratio of oxalic acid or the salt thereof is 0.1 to 10 times mole per mole of the nitrogen-containing compound. The enhancer composition is said to have an excellent stability with lapse of time to a change in temperatures and to markedly enhance the medicinal efficacy of an amino acid series herbicide even when the composition is used in a liquid form in combination with the herbicide. Again this does not diminish the unintended effects of glyphosate.

SUMMARY OF THE INVENTION

This invention solves the problem of increased disease pressure on plants and decreased crop yield following treatment of plants with glyphosate or the growing of the plants in soils to which glyphosate has been applied. According to the invention, aromatic amino acids are added to the plants or soil containing the and glyphosate in the soil is catabolized, preferably my microorganisms. The aromatic amino acids may preferably be added to the plant or soil before, during and/or after a glyphosate application to the plant and/or soil. If an accidental application of glyphosate to the crop is made, the combination of amino acids and microorganisms may be used to prevent herbicidal effects of glyphosate. Suitable microorganisms for catabolizing glyphosate according to the invention may be obtained by adding to the soil a yeast additive comprising *Saccharomyces cerevisiae*, leonardite/lignite, and naturally-occurring substances found in the yeast fermentation broth.

DETAILED DESCRIPTION OF PREFERRED EMBODIMENTS

Figure 1:
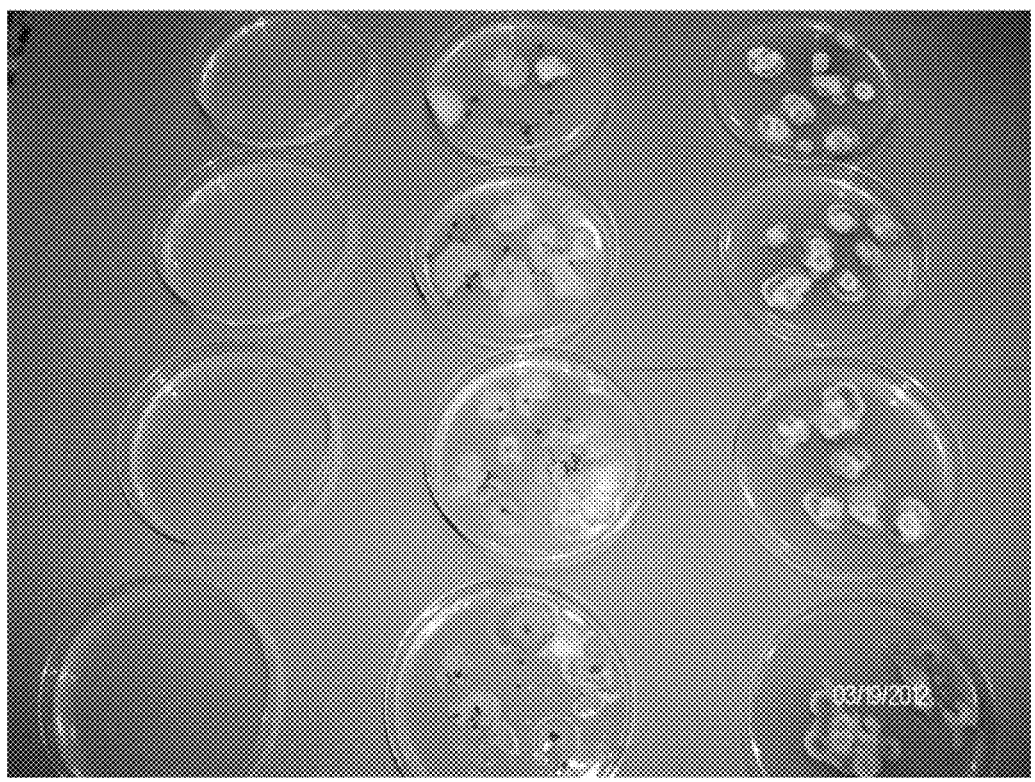
FIG. 1 is a photograph of petri dishes showing test results demonstrating that an additive of the invention is capable of catabolizing glyphosate pesticide.

Introduction:

The mode of action of glyphosate is inhibition of the enzyme 5 enolpyruvyl-shikimate-3-phosphatase synthase (EPSPS) in the shikimic acid pathway. This biochemical pathway is responsible for plant production of essential amino acids. Glyphosate is an effective herbicide because the compound remains intact in the plant with little degradation. Glyphosate is often described as exhibiting little or no activity in soil due to potential rapid adsorption on soil inorganic and organic particles.

However, some studies show that glyphosate is available in the soil after application, so then the glyphosate is available for uptake by plant roots, and microbial metabolism. The lingering glyphosate has often shown effects on economic yield of crops; some of these include yellowing of the foliage, increased disease pressure, and, economic yield lags.

This invention solves the problem of increased disease pressure and decreased yield by the addition of aromatic amino acids to the plant or soil along with microorganisms capable of catabolizing glyphosate. The aromatic amino acids may preferably be added to the plant or soil before, during and/or after a glyphosate application to the plant and/or soil. If an accidental application of glyphosate to the crop is made, the combination of amino acids and microorganism of the invention may be used to prevent the herbicidal effects of glyphosate.

Without the present invention, glyphosate acts as a selective biocide, having the consequence of important bacteria and fungi being challenged and removed from the soil profile after a glyphosate application. Exacerbating the effect of pesticides on plants is a further consequence—the chelation of micronutrients necessary for the ordinary enzymatic actions for plant cell production, maintenance, and immune system integrity. The combination of selecting out pathogenic fungi, lowering the beneficial bacteria counts, accumulating toxic concentrations of pesticide, and inhibition of mineral nutrition often becomes a deadly combination for viable plants, and gives rise to the need for the present invention.

Experiments

Recently, several reports have been made of disease in commodity crop production that cannot be cultured in the laboratory. This includes Citrus Greening. For instance, the disease Citrus Greening is often described ambiguously in literature as:

- citrus huanglongbing (HLB or citrus greening), is a highly destructive disease that has been spreading in both Florida and Brazil. HLB is a difficult disease to manage due to the nonspecific nature of disease symptoms, prolonged latency of the disease in field trees, probable irregular distribution of the pathogen in trees, effect of environment on symptom expression and possibly on bacterial multiplication, probable variations in tolerance to the bacterium in both the plant host and the vectors, and the fastidious nature of the bacterium. Even the most sensitive diagnostic tests available today are not adequate to certify a vector compromised tree as HLB-free. The tests can be treated only as confirmatory without much diagnostic value. A reliable plant-based diagnostic test probably would have to be based on a host systemic response specific to HLB, which presently is unknown.
- Visual symptoms and biological indexing have been the historical means of diagnosis of HLB. Still, detection systems are being developed using electron microscopy, HLB-specific fluorescent substance, and enzyme-linked immune sorbent assay (ELISA) with monoclonal antibodies. PCR based detection methods were developed based on sequences of the 16s ribosomal DNA and other regions of the bacterial genome. Sensitive detection methods for confirmation of symptoms developed include real-time quantitative PCR (qPCR) and loop-mediated isothermal amplification.
- There is no good source of genetic resistance to HLB in the genus *Citrus* or its relatives, and the disease cannot be controlled once the trees are infected. Management of HLB is dependent on prevention and reduction of inoculum in the field, achieved through the use of disease-free planting material (impossible), control of psyllid population in the groves (impossible), and timely removal of infected trees (impossible if infection cannot be determined). Because of limitations in the early detection of the disease, epidemiological models of the spread of HLB are based on symptoms (Visual), and assume a linear relationship between infection and symptom expression. HLB symptoms develop in about 20% of grafted plants within 3 to 12 months of graft inoculation under greenhouse conditions, but the same cannot be assumed for large trees under field situations. The latency period for the disease prior to symptom expression under field conditions is not clear, and information about the interval between psyllid inoculation of '*Ca. L. asiaticus*' in a field tree and the time when other psyllids can acquire the HLB bacteria from that tree is not available.

So then, the only argument for identification is 16S rRNA; however, there are two organelles found in many eukaryotic cells, mitochondria and chloroplasts (present in all plant cells), which contain ribosomes similar in size and makeup to those found in prokaryotes. This is one of many pieces of evidence that mitochondria and chloroplasts are themselves descended from free-living bacteria. With that we understand without growing bacterium in culture that it is impossible to assign infection via bacteria with 16S rRNA methods. Prior art literature has reported that, "The possibility exists that the HLB bacterium lacks vital gene functions that would allow it to grow in axenic culture. The intimate association of the HLB bacterium with its hosts may have permitted such gene functions to be provided by the host. In this case, it may be necessary to grow the HLB bacterium in co-culture with another organism that can provide the missing metabolites." This limitation argues against an exclusive role for this bacterium in HLB citrus greening disease.

Figure 2:
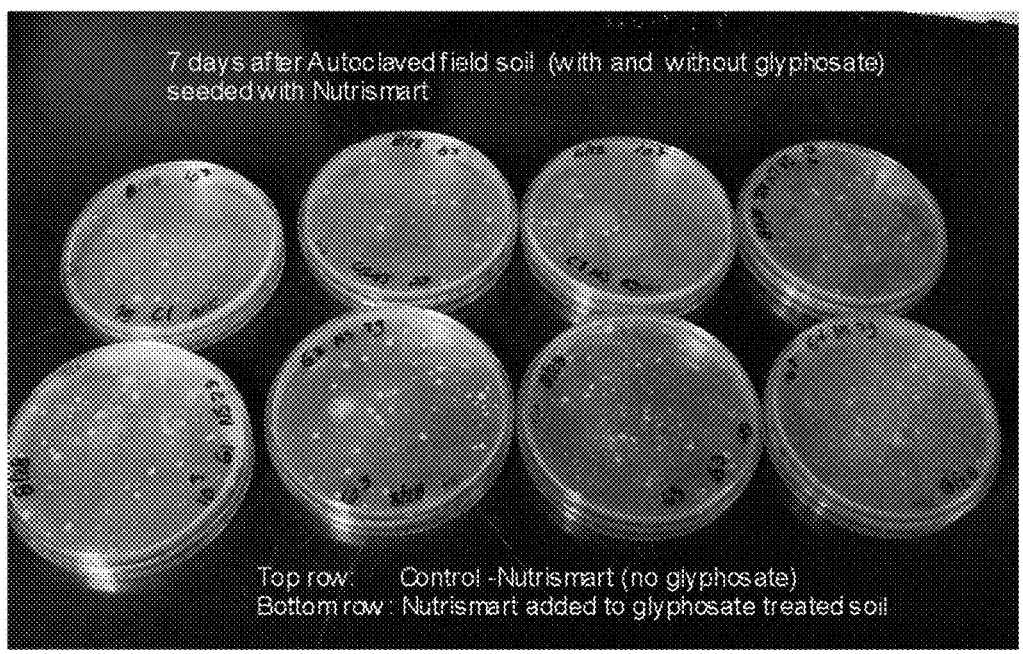
FIG. 2 is a photograph of petri dishes showing test results demonstrating that an additive of the invention is capable of catabolizing glyphosate pesticide in soil while promoting bacterial growth inhibited by glyphosate.

Contrary to prior art teachings, I have concluded HLB in Florida is a metabolic disease without a bacterial infection being a major cause. The available literature on the disease cannot be assimilated into a workable hypothesis that includes a bacterial infection as the major cause in my opinion. I have shown that microbial soil amendments with the capacity to catabolize pesticides remove all symptoms of the greening disease. The recovery of the orchard is accelerated when essential amino acids are applied to the plants.

Plants with Immune System Deficiencies:

Crops other than citrus also suffer nutrient deficiency and enzyme inhibition that prevents disease resistance as a result of glyphosate application. For instance, glyphosate inhibits production of essential amino acids. When those essential amino acids are placed in agar media the bacteria and fungi present in infected plant tissue fail to grow; in fact, they die. Similarly, when the media has chelated metal ions added, the fungi and bacteria fail to thrive. This is important in that simple compounds added to the media at ppm concentrations is enough to prevent disease from growing (spreading). It is simply the addition of the amino acids to agar that inhibits pathogens and draws a clear zone of inhibition; this implies the infection would not have occurred if the plant's essential amino acid production was viable and glyphosate was not present in the soil; the addition of ppm selected metal salts had the same effect.

EXAMPLES

Example 1

Growers typically spray 1 quart of a 39% glyphosate solution per acre, at a dilution of one quart in 20 gallons of water. That would be a dilution of 80 to 1, or 1.25%. Because I purchased a 25% glyphosate I had to make a concentration adjustment.

0.39/0.25=1.56 concentration difference.

So, 1.25*1.56=or 1.95% of the 25% glyphosate is the equivalent. In 300 ml mix of Difco Plate Count Agar, I added 6 ml of the 25% Glyphosate. As the agar cooled I dropped NutriSmart® additive into the media. Control on the left, SGN 150 center and SGN 250 on the right. (FIG. 1).

This experiment shows the ability of the NutriSmart® additive to catabolize the glyphosate pesticide. It appears the addition of glyphosate to the media selects out fungal populations commonly found in soil.

Example 2

An increase of 100× in overall bacterial activity after 7 days in soils seeded with NutriSmart® additive—both in glyphosate treated soil (4% solution) and soil with no added glyphosate. As seen in FIG. 2, the effect is slightly greater in the glyphosate added soil. The fungal presence appears fairly constant in both treatments.

This experiment shows the ability of the NutriSmart® additive to catabolize the glyphosate pesticide in soil while promoting bacterial growth inhibited by the glyphosate acting as a biocide. It appears the addition of glyphosate to the media selects out fungal populations commonly found in soil; while NutriSmart® additive promotes both fungal and bacterial growth. NutriSmart® additive reportedly is composed of *Saccharomyces cerevisiae* at $10^6$ cfu/g, starch, Leonardite/lignite, and, naturally-occurring substances found in the yeast fermentation broth. NutriSmart® additive supports and increases nitrogenase levels in the soil.

Example 3

Figure 3:
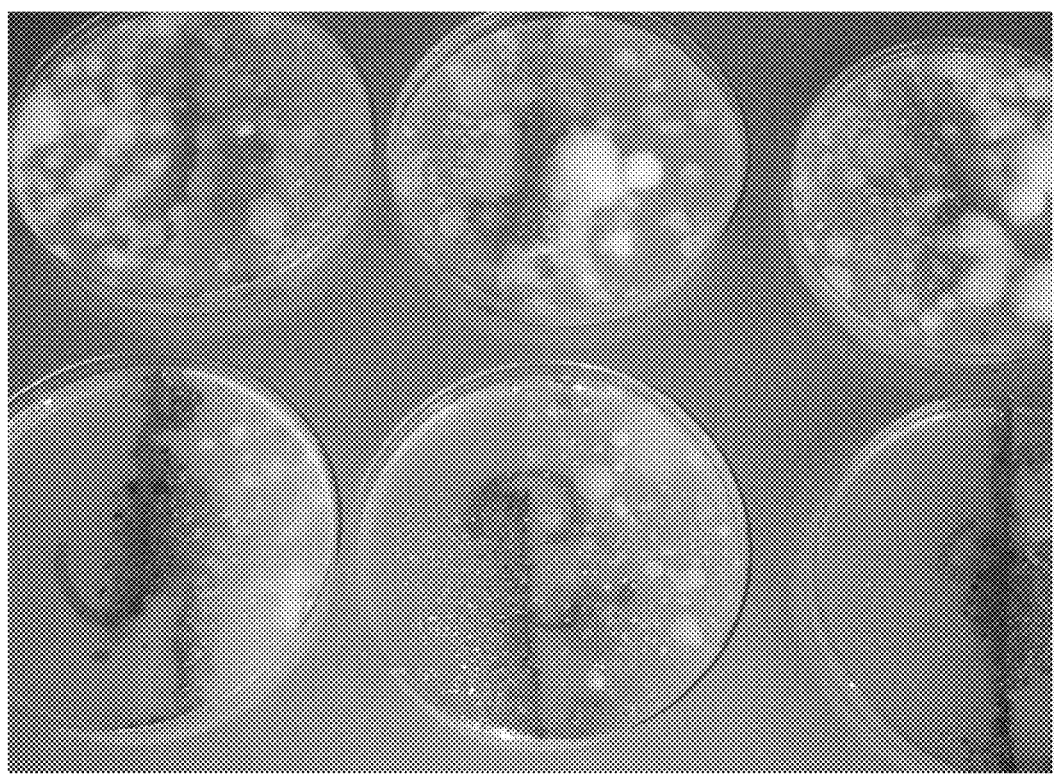
FIG. 3 is a photograph of petri dishes showing test results demonstrating that fungal and bacterial growth were inhibited by a plant with access to essential amino acids.

Tomato plants growing in glyphosate treated soil from Ohio had symptoms of disease. The sap from the stems of these plants was placed in Difco Plate Count Agar and bacteria and fungi prospered. However, the addition of essential amino acids at ppm concentrations was enough to inhibit the growth with strong lines of inhibition (FIG. 3). When the amino acids were replaced with a chelated metal solution the same line of inhibition was found. The amino acids added were Phenylalanine, Tyrosine, and Indole (a precursor to Tryptophan). The chelated metal solution consisted of 1% chelated nickel, 1.69% molybdic oxide and 0.24% selenium oxide.

This experimental breakthrough shows the pathogens present in the tomato plants could have been easily controlled by the plant itself if essential amino acid production had not been curtailed by prior use of pesticides that block plant essential amino acid biochemical pathway.

Example 4

In a field experiment a forty acre field was divided in half. The experiment was set up per the protocol below. Treatments were applied November 2012.
20 Acre Plot; 4×5 Acre Treatment Plots

| Treatment 1 | Treatment 2 | Treatment 3 | Treatment 4 |
| --- | --- | --- | --- |
| KaPre® proCreate | KaPre® proCreate | KaPre® proCreate | KaPre® proCreate |
| Nutrol® | Nutrol® | Nutrol® | Nutrol® |
| NutriSmart® | NutriSmart® | NutriSmart® | NutriSmart® |
|  | Semonia Concentrate | Semonia Concentrate | Semonia Concentrate |
|  |  | 3 Amigos | 3 Amigos |
|  |  |  | KaPre Argosy |

| Foliar Product Requirements | | | |
| --- | --- | --- | --- |
| Foliar Apply | Rate/Acre | Number of Acres | Amount Needed |
| KaPre® proCreate | ½ Gallon | 20 | 10 Gallons |
| Nutrol® | 3 Pounds | 20 | 60 Pounds |
| Semonia Concentrate | ½ Gallon | 15 | 7.5 Gallons |
| 3 Amigos | 1 Gallon | 10 | 10 Gallons |
| KaPre Argosy | 1¼ Gallon | 5 | 1¼ Gallons |

| Soil-Applied Product Requirements | | | |
| --- | --- | --- | --- |
| Soil Apply | Rate/Acre | Number of Acres | Amount Needed |
| KaPre® proCreate (through Irrigation) | ½ Gallon | 20 | 10 Gallons |
| NutriSmart® | 200 Pounds | 20 | 4,000 Pounds |
| Semonia Concentrate (through Irrigation) | ½ Gallon | 15 | 7.5 Gallons |

Figure 4:
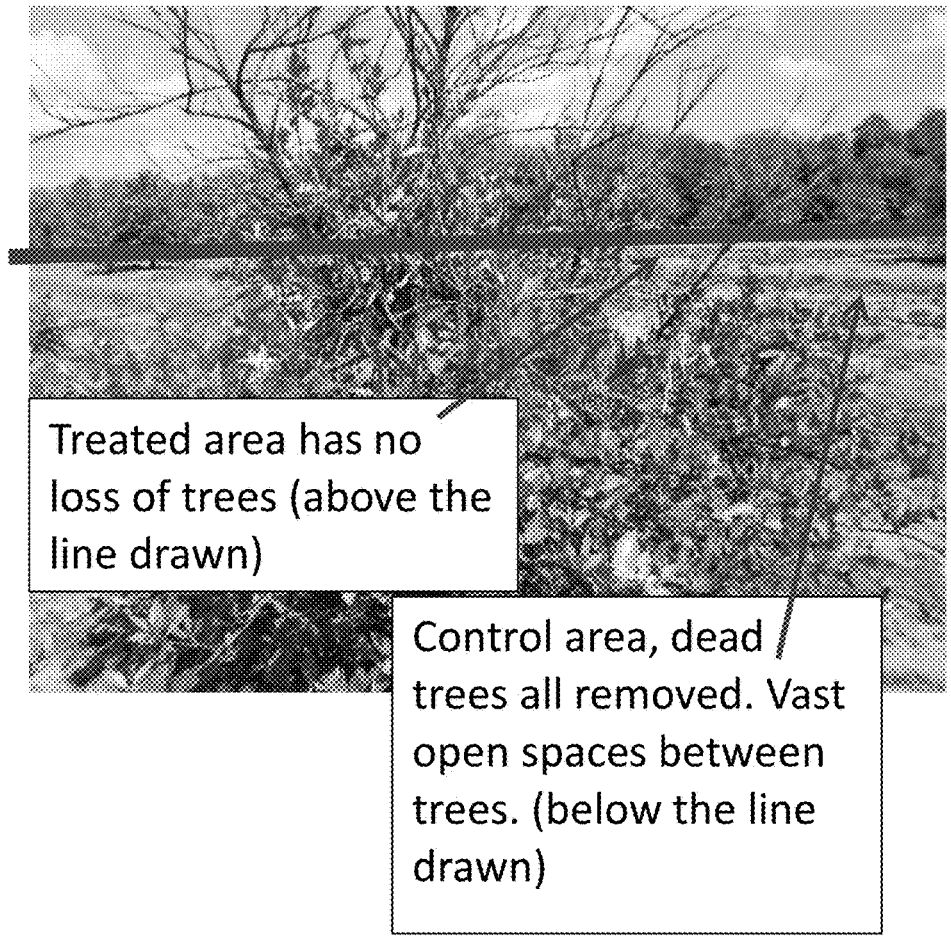
FIG. 4 is a photograph of field test results showing plants treated according to the invention resisted citrus greening disease, while untreated plants did not.
Figure 5:
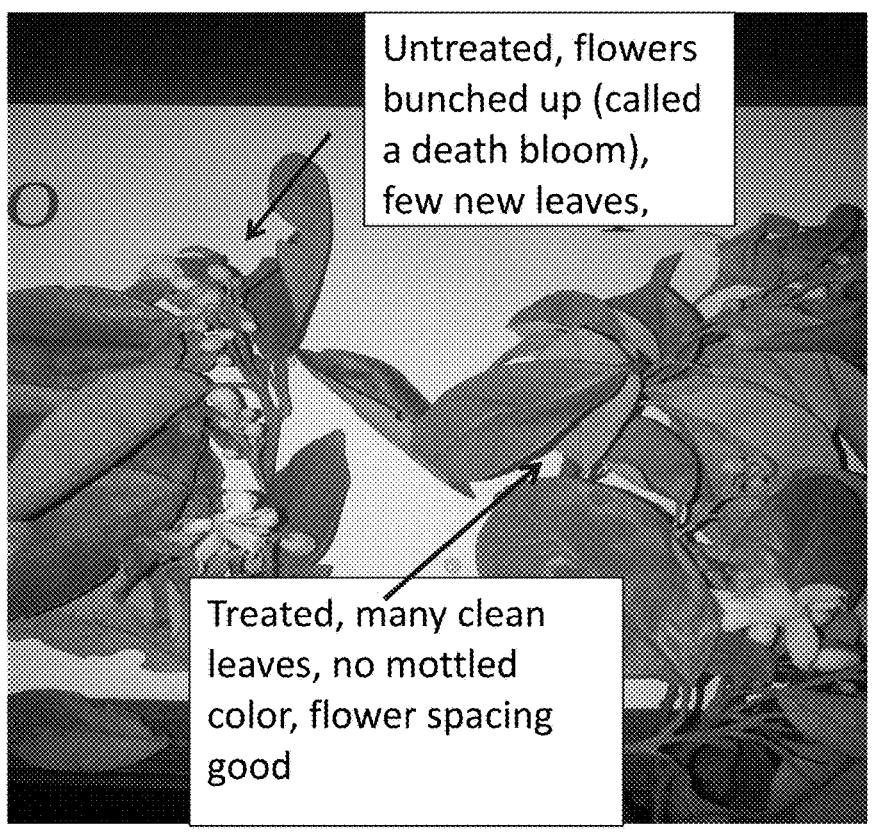
FIG. 5 is a photograph of plant leaves from the field test of FIG. 4, indicating that the treated plants had normal, healthy leaves while the untreated plants did not.

All trees in the orchard treated with NutriSmart® additive flourished with no sign of citrus greening disease (FIGS. 4 and 5); in fact, four months after treatment all symptoms of Citrus Greening disease are absent in the treated areas and present in the non-treated areas.

In an effort to address the published prior art information about citrus greening, the evidence shown here, when considered with the prior art literature, leads to the conclusion that citrus greening disease is probably not a bacterial infection. No bacteria have been found or cultured for the malady; only morphology and color changes have been reported. Without wishing to be limited by theory, it is my belief the citrus crops are suffering from cultural practices that promote changes in the soil microbial populations, buildup of pesticides from repeated applications in soil ill-equipped to catabolize, and simply an event such as a fertilizer application that desorbs the pesticides at high concentrations that produce a toxic environment for the trees or other plants. The absorption of the dissolved pesticides block the trees/plant ability to produce essential amino acids and from that morphological changes in the leaves, flowers, and fruit are apparent.

When NutriSmart® additive is applied to the soil the beneficial microbes are replenished, microbes capable of bioremediation of pesticides flourish and the orchards regain their health; while the applications of foliar essential amino acids replenish the amino acid pool and morphology reverts to normal.

Preferred aromatic amino acids for use in the invention may be selected from the group consisting of phenylalanine, tyrosine, and tryptophane, and the phenolic derivatives of phenylalanine, tyrosine, and tryptophane, used alone or in combination.

As used herein, the following trademarked products may be obtained from the companies indicated:

KaPre® procreate, is a registered trademark of Lido-Chem, Inc., and the product is available from LidoChem, Inc. in Hazlet, N.J., consisting of 7.8% urea phosphite, 1% Zn, 0.25% Mn, 0.125% Cu and 0.025% B, and $10^7$ cfu's/ml *Bacillus amyloliquefaciens*.

Nutrol®, is a registered trademark of LidoChem, Inc., and the product is available from LidoChem, Inc. in Hazlet, N.J.

NutriSmart®, is a registered trademark of CK Life Sciences Int'l., (Holdings) Inc., and the product is available from LidoChem, Inc. in Hazlet, N.J. Visually, the NutriSmart® additive encourages what appears to be *Trichoderma* species in petri dishes, particularly, *T. viride* and *Trichoderma harzianum*.

Semonia Concentrate, is a product available from Lido-Chem, Inc. in Hazlet, N.J., consisting of 1% chelated nickel, 1.69% molybdic oxide and 0.24% selenium oxide.

3 Amigos, is a product available from LidoChem, Inc in Hazlet, N.J., consisting of Phenylalanine, Tyrosine, and Indole (a precursor to Tryptophan).

KaPre Argosy, is a product available from LidoChem, Inc. in Hazlet, N.J.

Discussion of Possible Components for Admixes:

For practical application, the aromatic amino acids for use according to this invention may be used or applied alone or may generally form part of formulations which also comprise a support and/or a surfactant in addition to active materials.

In the context of the invention, a support is an organic or mineral, natural or synthetic material, with which the active material is associated to facilitate its application, for example, in the case of fertilizer, fungicides and herbicides, to the plant, to seeds or to soil, or to facilitate its transportation or handling. The support can be solid (e.g. clays, natural or synthetic silicates, resins, waxes, solid fertilizer and fungicides) or fluid (e.g., water, alcohols, ketones, petroleum fractions, chlorinated hydrocarbons, liquefied gases, liquid fertilizer and fungicides). When a surfactant is used, the surfactant can be an ionic or non-ionic emulsifier, dispersant or wetting agent such as, for example, salts of polyacrylic acids and lignin-sulphonic acids, condensates of ethylene oxide with fatty alcohols, fatty acids or fatty amines.

The compositions comprising the amino acids of the present invention can be prepared in the form of wettable powders, soluble powders, dusting powders, granulates, solutions, emulsifiable concentrates, emulsions, suspended concentrates and aerosols.

The wettable powders according to the invention can be prepared in such a way that they contain the active material, and they often or typically contain, in addition to a solid support, a wetting agent, a dispersant and, when necessary, one or more stabilizers and/or other additives, such as, for example, penetration agents, adhesives or anti-lumping agents, colorants etc.

Aqueous dispersions and emulsions, such as, for example, compositions comprising the compounds of this invention obtained by diluting with water a wettable powder or an emulsifiable concentrate are also included within the general scope of the invention. These emulsions can be of the water-in-oil type or of the oil-in-water type, and can have a thick consistency resembling that of a "mayonnaise".

The compositions comprising the compounds of the present invention can contain other ingredients, for example protective colloids, adhesives or thickeners, thixotropic agents, stabilizers or sequestrants, as well as other active materials. A modest list of examples of possible formulation components for inclusion with the compositions of this invention follows without limitation.

The supposed function of this component is to supply carbon skeleton for synthesis of proteins and other molecules or to supply energy for metabolism. Water-soluble carbohydrates such as sucrose, fructose, glucose and other di- and monosaccharides are suitable, commonly in the form of molasses or other by-products of food manufacture. Commercially available lignosulfonates, discussed below under the heading "Complexing Agents," are also suitable as a CSE source inasmuch as they commonly contain sugars.

CSE Components:

Sugar—mannose, lactose, dextrose, erythrose, fructose, fucose, galactose, glucose, gulose, maltose, polysaccharide, raffinose, ribose, ribulose, rutinose, saccharose, stachyose, trehalose, xylose, xylulose, adonose, amylose, arabinose, fructose phosphate, fucose-p, galactose-p, glucose-p, lactose-p, maltose-p, mannose-p, ribose-p, ribulose-p, xylose-p, xylulose-p, deoxyribose, corn steep liquor, whey, corn sugar, corn syrup, maple syrup, grape sugar, grape syrup, beet sugar, sorghum molasses, cane molasses, calcium lignosulfonate sugar alcohol—adonitol, galactitol, glucitol, maltitol, mannitol, mannitol-p, ribitol, sorbitol, sorbitol-p, xylitol xxxx acids—glucuronic acid, a-ketoglutaric acid, galacturonic acid, glutaric acid, gluconic acid, pyruvic acid, poly galacturonic acid, saccharic acid, citric acid, succinic acid, malic acid, oxaloacetic acid, aspartic acid, phosphoglyceric acid, fulvic acid, ulmic acid, humic acid, glutamic acid.

Nucleotides and bases—adenosine, adenosine-p, adenosine-p-glucose, uridine, uridine-p, uridine-p-glucose, thymine, thymine-p, cytosine, cytosine-p, guanosine, guanosine-p, guanosine-p-glucose, guanine, guanine-p, NADPH, NADH, FMN, FADH.

The Macronutrient Components:

The macronutrients are essential to nutrition and growth. The most important macronutrients are N, P and K. Some example nitrogen compounds are: ammonium nitrate, mono-ammonium phosphate, ammonium phosphate sulfate, ammonium sulfate, ammonium phosphatenitrate, diammonium phosphate, ammoniated single superphosphate, ammoniated triple superphosphate, nitric phosphates, ammonium chloride, aqua ammonia, ammonia-ammonium nitrate solutions, calcium ammonium nitrate, calcium nitrate, calcium Cyanamid, sodium nitrate, urea, urea-formaldehyde, urea-ammonium nitrate solution, nitrate of soda potash, potassium nitrate, amino acids, proteins, nucleic acids.

Example Phosphate sources include: superphosphate (single, double and/or triple), phosphoric acid, ammonium phosphate, ammonium phosphate sulfate, ammonium phosphate nitrate, diammonium phosphate, ammoniated single superphosphate, ammoniated single superphosphate, ammoniated triple superphosphate, nitric phosphates, potassium pyrophosphates, sodium pyrophosphate, nucleic acid phosphates and phosphonic and phosphorous acid derivatives.

The potassium ion for example can be found in: potassium chloride, potassium sulfate, potassium gluconate, sulfate of potash magnesia, potassium carbonate, potassium acetate, potassium citrate, potassium hydroxide, potassium manganate, potassium phosphate, potassium molybdate, potassium thiosulfate, potassium zinc sulfate and the like.

Calcium sources include for example: calcium ammonium nitrate, calcium nitrate, calcium Cyanamid, calcium acetate, calcium acetylsalicylate, calcium borate, calcium borogluconate, calcium carbonate, calcium chloride, calcium citrate, calcium ferrous citrate, calcium glycerophosphate, calcium lactate, calcium oxide, calcium pantothenate, calcium propionate, calcium saccharate, calcium sulfate, calcium tartrate and the like.

Magnesium can be found for example in: magnesium oxide, dolomite, magnesium acetate, magnesium benzoate, magnesium bisulfate, magnesium borate, magnesium chloride, magnesium citrate, magnesium nitrate, magnesium phosphate, magnesium salicylate, magnesium sulfate.

Sulfur containing compounds include for example: ammonium sulfate, ammonium phosphate sulfate, calcium sulfate, potassium sulfate, magnesium sulfate, sulfuric acid, cobalt sulfate, copper sulfate, ferric sulfate, ferrous sulfate, sulfur, cysteine, methionine and elemental sulfur.

Micronutrient Components:

The most important micronutrients are or comprise: Zn, Fe, Cu, Mn, B, Co, Se, and Mo.

Vitamin/Cofactor Components:

The most important are folic acid, biotin, pantothenic acid, nicotinic acid, riboflavin and thiamine and include for example: Thiamine—thiamine pyrophosphate, thiamine monophosphate, thiamine disulfide, thiamine mononitrate, thiamine phosphoric acid ester chloride, thiamine phosphoric acid ester phosphate salt, thiamine 1,5 salt, thiamine tri phosphoric acid ester, thiamine tri phosphoric acid salt, yeast, yeast extract Riboflavin—riboflavin acetyl phosphate, flavin adenine dinucleotide, flavin adenine mononucleotide, riboflavin phosphate, yeast, and, yeast extract. Nicotinic acid—nicotinic acid adenine dinucleotide, nicotinic acid amide, nicotinic acid benzyl ester, nicotinic acid monoethanolamine salt, yeast, yeast extract, nicotinic acid hydrazide, nicotinic acid hydroxamate, nicotinic acid-N-(hydroxymethyl)amide, nicotinic acid methyl ester, nicotinic acid mononucleotide, nicotinic acid nitrile. Pyridoxine—pyridoxal phosphate, yeast, yeast extract Folic acid—yeast, yeast extract, folinic acid. Biotin-biotin sulfoxide, yeast, yeast extract, biotin 4-amidobenzoic acid, biotin amidocaproate N-hydroxysuccinimide ester, biotin 6-amidoquinoline, biotin hydrazide, biotin methyl ester, d-biotin-N-hydroxysuccinimide ester, biotin-maleimide, d-biotin p-nitrophenyl ester, biotin propranolol, 5-(N-biotinyl)-3 aminoallyl)-uridine 5'-triphosphate, biotinylated uridine 5'-triphosphate, N-e-biotinyl-lysine. Pantothenic acid—yeast, yeast extract, coenzyme A, Cyanocobalamin—yeast, yeast extract. Phosphatidylcholine-soybean oil, eggs bovine heart, bovine brain, bovine liver, L-a-phosphatidylcholine, B-acetyl-g-O-alkyl, D-a-phosphatidyl choline (PTCn), B-acetyl-g-O-hexadecyl, DL-a-PTCh, B-acetyl-g-O-hexadecyl, L-a-PTCh, B-acetyl-g-O-(octadec-9-cis-enyl), L-a-PTCh, B-arachidonoyl, g-stearoyl, L-a-PTCh, diarachidoyl, L-a-PTCh, dibehenoyl (dibutyroyl, dicaproyl, dicapryloyl, didecanoyl, dielaidoyl, 12 diheptadecanoyl, diheptanoyl), DL-a-PTCh dilauroyl, L-a-PTCh dimyristoyl (dilauroyl, dilinoleoyl, dinonanoyl, dioleoyl, dipentadeconoyl, dipalmitoyl, distearoyl, diundecanoyl, divaleroyl, B-elaidoyl-a-palmitoyl, B-linoleoyl-a-palmitoyl) DL-a-PTCh di-O-hexadecyl (dioleoyl, dipalmitoyl, B—O-methyl-g-O-hexadecyl, B-oleoyl-g-O-hexadecyl, B-palmitoyl-g-O-hexadecyl), D-a-PTCh dipalmitoyl, L-a-PTCh, B—O-methyl-g-O-octadecyl, L-a-PTCh, B—(NBD-aminohexanoyl)-g-palmitoyl, L-a-PTCh, B-oleoyl-g-O-palmitoyl (stearoyl), L-a-PTCh, B-palmitoyl-g-oleoyl, L-a-PTCh, B-palmitoyl-a-(pyren 1-yl) hexanoyl, L-a-PTCh, B(pyren-1-yl)-decanoyl-g-palmitoyl, L-a-PTCh, B-(pyren-1-yl)-hexanoyl-g-palmitoyl, L-a-PTCh, B-stearoyl-g-oleoyl. Inositol—inositol monophosphate, inositol macinate, myo-inositol, epi-inositol, myo-inositol 2,2'anhydro-2-c-hydroxymethyl (2-c-methylene-myoinositol oxide), D-myo-inositol 1,4-bisphosphate, DL-myo-inositol 1,2-cyclic monophosphate, myo-inositol dehydrogenase, myo-inositol hexanicotinate, inositol hexaphosphate, myo-inositol hexasulfate, myo-inositol 2-monophosphate, D-myo-inositol 1-monophosphate, DL-myo-inositol 1-monophosphate, D-myo-inositol triphosphate, scyllo-inositol PABA—m-aminobenzoic acid, O-aminobenzoic acid, p-aminobenzoic acid butyl ester, PABA ethyl ester, 3-ABA ethyl ester.

Complexing Agents:

The function of this component, particularly in agricultural applications, aside from its proposed use as a Carbon skeleton agent, is to solubilize other components of the composition which otherwise may precipitate and become assailable or may immobilize minerals in the soil which might otherwise be unavailable to flora and fauna. Complexing agents such as, for example, citric acid, humic acids, lignosulfonate, etc. serve to tie up ions such as iron and prevent them from forming precipitates. In some cases this complexing is by way of chelation. These agents may form complexes with the following compounds for example: Citric acid; Ca, K, Na and ammonium lignosulfonates, fulvic acid, ulmic acid, humic acid, Katy-J, EDTA, EDDA (ethylenediaminedisuccinic acid), EDDHA, HEDTA, CDTA, PTPA, NTA, MEA, IDS, EDDS, and 4-phenylbutyric acid.

Other complexing agents include for example: Al and its salts, Zn—zinc oxide, zinc acetate, zinc benzoate, zinc chloride, zinc citrate, zinc nitrate, zinc salicylate, ziram Ni compounds, Fe—ferric chloride, ferric citrate, ferric fructose, ferric glycerophosphate, ferric nitrate, ferric oxide (saccharated), ferrous chloride, ferrous citrate ferrous fumarate, ferrous gluconate, ferrous succinate. Mn—manganese acetate, manganese chloride, manganese nitrate, manganese phosphate, Cu—cupric acetate, cupric butyrate, cupric chlorate, cupric chloride, cupric citrate, cupric gluconate, cupric glycollate, cupric nitrate, cupric salicylate, cuprous acetate, cuprous chloride. B—calcium borate, potassium borohydride, borax, boron trioxide, potassium borotartrate, potassium tetraborate, sodium borate, sodium borohydride, sodium tetraborate and boric acid. Mo—molybdic acid, calcium molybdate, potassium molybdate, sodium molybdate. Co—cobaltic acetate, cobaltous acetate, cobaltous chloride, cobaltous oxalate, cobaltous potassium sulfate, cobaltous sulfate, and selinates.

Growth Regulators:

Seaweed extract—kelp extract, Kinetin, Kinetin riboside, benzyladenine, zeatin riboside, zeatin, extract of corn cockle, isopentenyl adenine, dihydrozeatin, indoleacetic acid, phenylacetic acid, IBA, indole ethanol, indole acetaldehyde, indoleacetonitrile, indole derivatives, gibberellins (e.g. GA1, GA2, GA3, GA4, GA7, GA38 etc.) polyamines, monoethanolamine, allopurinol, GA inhibitors, ethylene inducing compounds, ethylene biosynthesis inhibitors, GABA, anticytokinins and antiauxins, ABA inducers and inhibitors, and other known growth regulators.

Gum Components:

Xanthan gum—guar gum, gum agar, gum accroides, gum arabic, gum carrageenan, gum damar, gum elemi, gum ghatti, gum guaiac, gum karya, locust bean gum, gum mastic, gum pontianak, gum rosin, gum storax, gum tragacanth Microbialstats, Proprionic Acid, Benzoic Acid, Sorbic Acid, Proteins and Amino Acids.

Buffers

Phosphate buffer, formate or acetate buffer, AMP buffer, calcium tartrate, glycine buffer, phosphate citrate buffer, tris buffer, ECT.

If desired, a formulation or composition of the present invention may also include beneficial microorganisms.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention.

Accordingly, the scope of protection is not limited by the description set out above, including the claims, and that scope includes all equivalents of the subject matter of the claims. Each and every claim is incorporated into the specification as an embodiment of the present invention. Thus, the claims are a further description and are an addition to the preferred embodiments of the present invention. The disclosures of the references cited herein are hereby incorporated by reference, to the extent that they provide exemplary, procedural, or other details supplementary to those set forth herein.

I claim:

1. A method for ameliorating the herbicide effect on plants from a glyphosate application to the plants or soil containing the plants, wherein glyphosate inhibits production of amino acids by the plants, the method comprising: applying to the plants or soil containing the plants, an aromatic amino acid from the group consisting of phenylalanine, tyrosine, tryptophan, and phenolic derivatives of phenylalanine, tyrosine, tryptophan, and combinations thereof, and a yeast additive comprising *Saccharomyces cerevisiae* yeast at $10^6$ cfu/g, starch and leonardite/lignite, such that the amino acids that the glyphosate inhibits the plants from producing are replenished.

2. The method of claim 1 wherein the aromatic amino acid is applied to the plant before the glyphosate application.

3. The method of claim 1 wherein the aromatic amino acid is applied to the plant during the glyphosate application.

4. The method of claim 1 wherein the aromatic amino acid is applied to the plant after the glyphosate application.

5. The method of claim 1 wherein the aromatic amino acid is included in an admix.

6. The method of claim 1 further comprising applying to the soil containing the plants microbes capable of catabolizing glyphosate and wherein the glyphosate in the soil is catabolized by the microbes.

7. The method of claim 1 wherein the aromatic amino acid applied restores the amino acid pool within the plant and blocked by the application of glyphosate, thereby restoring healthy morphology to the plant.

8. The method of claim 1 further comprising adding an Admix to the soil.

9. The method of claim 1 wherein the yeast additive supports and increases nitrogenase levels in the soil.

10. The method of claim 1 wherein the yeast additive results in the catabolizing of glyphosate in the soil.

* * * * *